(12) United States Patent
Park et al.

(10) Patent No.: US 10,774,351 B2
(45) Date of Patent: Sep. 15, 2020

(54) **METHOD FOR PREPARING ANTHOCYANIN OLIGOMERS BY USING COENZYME DERIVED FROM *ASPERGILLUS* SP. STRAIN**

(71) Applicants: Pyo-Jam Park, Chungju-si (KR); Tuk-Rai Jeong, Seongnam-si (KR); Hyun-Pil Yang, Pyeongtaek-si (KR); Jin Woo Hwang, Chungju-si (KR)

(72) Inventors: Pyo-Jam Park, Chungju-si (KR); Tuk-Rai Jeong, Seongnam-si (KR); Hyun-Pil Yang, Pyeongtaek-si (KR); Jin Woo Hwang, Chungju-si (KR)

(73) Assignee: KITTO LIFE, Pyeongtaek-si (KR)

( * ) Notice: Subject to any disclaimer, the term of this patent is extended or adjusted under 35 U.S.C. 154(b) by 0 days.

(21) Appl. No.: 16/046,012

(22) Filed: Jul. 26, 2018

(65) Prior Publication Data

US 2018/0327795 A1 Nov. 15, 2018

Related U.S. Application Data

(63) Continuation of application No. PCT/KR2016/008429, filed on Aug. 1, 2016.

(30) Foreign Application Priority Data

Jan. 27, 2016 (KR) .......................... 10-2016-0010085

(51) Int. Cl.
| | | |
|---|---|---|
| *C12P 17/16* | (2006.01) | |
| *C12P 17/06* | (2006.01) | |
| *C12P 19/60* | (2006.01) | |
| *C12N 9/24* | (2006.01) | |
| *C12N 1/16* | (2006.01) | |
| *C12R 1/685* | (2006.01) | |

(52) U.S. Cl.
CPC .............. *C12P 17/162* (2013.01); *C12N 1/16* (2013.01); *C12N 9/24* (2013.01); *C12P 17/06* (2013.01); *C12P 19/60* (2013.01); *C12R 1/685* (2013.01)

(58) Field of Classification Search
CPC .. C12R 1/685; C12N 1/16; C12N 9/24; C12P 17/06; C12P 17/162; C12P 19/60
See application file for complete search history.

(56) References Cited

U.S. PATENT DOCUMENTS 6,800,433 B1 * 10/2004 Honda ................. C07D 311/62 435/18

FOREIGN PATENT DOCUMENTS

| CN | 101255453 A | 9/2008 |
|---|---|---|
| DE | 3622818 A1 | 1/1987 |
| JP | 2012213358 A | 11/2012 |
| JP | 2013159603 A | 8/2013 |
| KR | 1020120079040 A | 7/2012 |
| KR | 101182630 B1 | 9/2012 |

OTHER PUBLICATIONS

Dulf et al., Total phenolic contents, antioxidant activities, and lipid fractions from berry pomaces obtained by solid-state fermentation of two *Sambacus* species with *Aspergillus niger*. J. Agric. food Chem., 2015, vol. 63: 3489-3500. (Year: 2015).*
Mondal et al., Affinity precipitation of *Aspergillus niger* pectinase by microwave-treated alginate. Prot. Express. Purification., 2004, vol. 33: 104-109. (Year: 2004).*
Gama et al., Optimisation of enzymatic hydrolysis of apple pomace for production of biofuel and biorefinery chemicals using commercial enzymes. 3 Biotech, 2015, vol. 5: 1075-1087. (Year: 2015).*
Lee et al., Studies related to changes in the extraction of phenolics and color characteristics due to enzyme treatment during fermentation of red wine (*Muscat bailey* A). The Korean J. Food & Nutrition. 2010, vol. 23(3): 324-331; English Translation. (Year: 2010).*
Viscozyme L: 3 pages downloaded from https://www.sigmaaldrich.com/, Aug. 16, 2019 (Year: 2019).*
Pricelius, Sina; Substrate specificities of glycosidases from *Aspergillus* species pectinase preparations on elderberry anthocyanins; Journal of Agricultural and Food Chemistry; 2009, 57, 3, 1006-1012.
Yan, Yajun; Metabolic engineering of anthocyanin biosynthesis in *Escherichia coli*; Applied and Environmental Microbiology; 2005, 71, 7, 3617-3623.
Toshiki Minetoki et al, Aspergillus, Chemistry and Biology, vol. 38, No. 12, 2000, pp. 831-838 (9 pages).
Jonghyun Lee et al., Purified high-dose anthocyanoside oligomer administration improves nocturnal vision and clinical symptoms in myopia subjects; British Journal of Nutrition (2005) 93, 895-899 (5 pages).
"Coenzyme," Biochemistry Dictionary (3rd edition), Tokyo Chemical Co., Ltd., Jul. 1, 2000, pp. 1296-1297 (2 pages).
"Fermentation," Biochemistry Dictionary (3rd edition), Tokyo Chemical Co., Ltd., Jul. 1, 2000, pp. 1062-1063 (2 pages).

(Continued)

*Primary Examiner* — Ganapathirama Raghu
(74) *Attorney, Agent, or Firm* — Reinhart Boerner Van Deuren P.C.

(57) ABSTRACT

The present invention relates to a method of preparing an anthocyanin oligomer using a coenzyme derived from an *Aspergillus* sp. strain, and more particularly to a method of preparing an anthocyanin oligomer by fermenting an anthocyanin monomer with a coenzyme of *Aspergillus niger*, which is a kind of *Aspergillus* sp. strain. According to the present invention, in order to overcome contamination problems during the culturing process using *Aspergillus niger*, a coenzyme of *Aspergillus niger* is extracted and the fermentation process is performed using the same, whereby an anthocyanin oligomer characterized by reduced concern of contamination and superior radical-scavenging effects, compared to existing anthocyanin monomers, can be produced. Also, an anthocyanin oligomer, obtained through fermentation using glucosidase as an enzyme contained in the coenzyme, can exhibit excellent fermentation efficiency and radical-scavenging ability, and polymerization of the anthocyanin oligomer can be confirmed even upon the fermentation of the enzyme including glucosidase.

1 Claim, 15 Drawing Sheets

(56) References Cited

OTHER PUBLICATIONS

Kozo Asano et al., A Method of Softening Soybean Changing their Hardness after Steam-Heating with a Modified Dipping Aqueous Solutions; No. 1, 1994 (7 pages).

* cited by examiner

METHOD FOR PREPARING ANTHOCYANIN OLIGOMERS BY USING COENZYME DERIVED FROM *ASPERGILLUS* SP. STRAIN

CROSS-REFERENCE TO RELATED PATENT APPLICATIONS

This patent application is a continuation of PCT Application No. PCT/KR2016/008429, filed Aug. 1, 2016, which claims priority to Korean Patent Application No. 10-2016-0010085, filed Jan. 27, 2016, the entire contents of which is incorporated herein for all purposes by this reference.

TECHNICAL FIELD

The present invention relates to a method of preparing an anthocyanin oligomer using a coenzyme derived from an *Aspergillus* sp. strain, and more particularly to a method of preparing an anthocyanin oligomer by fermenting an anthocyanin monomer with a coenzyme of *Aspergillus niger*, which is a kind of *Aspergillus* sp. strain, and with glucosidase, which is an enzyme contained in the coenzyme.

BACKGROUND ART

Anthocyanin functions as a natural pigment and also exhibits various physiological activities, such as an antioxidant function, reduction of a cholesterol level, improvement of vision, vascular protection, prevention of arteriosclerosis and heart disease, an anti-ulcer function, an anticancer function, an anti-inflammation function, diabetes suppression, protection from UV radiation, etc. Furthermore, anthocyanin is actively utilized in medicines and is thus receiving attention as a new material for producing health foods and new medicines.

Anthocyanin is unstable in neutral or alkaline solutions, and gradually becomes decolorized when exposed to light even in an acidic solution, and is thus considered to be a structurally unstable material. In particular, factors affecting the stability of an anthocyanin pigment include the chemical structure of anthocyanin, the concentration of the pigment, the pH of the solution, the temperature, the presence or absence of a coexisting pigment, metal ion, enzyme, oxygen, ascorbic acid, sugar, and the like, and the maintenance of chromaticity, that is, the structural stability thereof may vary depending on variation in these factors. Because of this structural instability, many difficulties are encountered in active utilization as foods and medicines, and studies are under way to improve the stability of anthocyanin.

Anthocyanin contained in most food materials is in a monomer form, which is unstable at neutral and alkaline pH and is also weakly resistant to light and heat. The polymer form is present in small amounts in foods but has higher functionality and stability than the monomer, and the typical antioxidant function thereof is also doubled. Recently, research into anthocyanin oligomers that improve subjective symptoms and contrast sensitivity in cases of myopia and amblyopia has been reported.

Related techniques include Korean Patent No. 10-1182630 (Sep. 7, 2012), Korean Patent Application Publication No. 10-2012-0079040 (Jul. 11, 2012), etc.

*Aspergillus* sp. mold is a useful microorganism for producing enzymes, organic acids and metabolites having pharmacological activity. It has been usefully employed in agriculture as well as in the food industry, the liquor industry, and the pharmaceutical industry, and has been used for producing traditional fermented foods for a long time, and is therefore recognized as a safe strain. Furthermore, since fungi have many exo-enzymes that are secreted to the outside and have a variety of functions, they may be used to economically produce useful materials by means of natural enzymes. There have been conventional reports for the production of anthocyanin oligomers using *Aspergillus* sp. mold, but the direct use of the strain is problematic in that contamination may occur in the course of production of anthocyanin oligomers.

In order to confirm whether an anthocyanin oligomer may be prepared using an enzyme that is secreted to the outside, without direct use of an *Aspergillus* sp. strain, the present inventors have devised methods of producing an anthocyanin oligomer using a coenzyme extracted from a culture media of an *Aspergillus niger* stain and also using as an enzyme glucosidase obtained by analyzing the coenzyme and a multi-enzyme complex containing a wide range of carbohydrases, including arabanase, cellulase, β-glucanase, hemicellulase, and xylanas (commercially available under the trade name Viscozyme® L from Novozymes Corp.), and have ascertained the efficacy thereof, thus culminating in the present invention.

BRIEF SUMMARY

Accordingly, the present invention is intended to provide a method of economically producing an anthocyanin oligomer by synthesizing an anthocyanin oligomer using a coenzyme of *Aspergillus niger* and also using as an enzyme glucosidase obtained by analyzing the coenzyme and the multi-enzyme complex containing a wide range of carbohydrases (Viscozyme® L).

Therefore, the present invention provides a method of preparing an anthocyanin oligomer, comprising: (1) isolating a water-soluble coenzyme from a culture media of an *Aspergillus* sp. strain; and (2) fermenting an anthocyanin monomer with the coenzyme isolated in step (1).

Preferably, the *Aspergillus* sp. strain in step (1) is *Aspergillus niger*.

Preferably, the strain in step (1) is cultured at a temperature of 15 to 30° C. for 4 to 8 days.

Preferably, the coenzyme in step (1) is isolated as an enzyme by adding the culture media with an organic solvent to give a precipitate and dissolving the precipitate in distilled water.

Preferably, the fermenting in step (2) includes mixing the anthocyanin monomer and distilled water at a mass ratio of 1:8 to 1:15 to prepare an anthocyanin monomer solution, after which mixing the anthocyanin monomer solution and the coenzyme isolated in step (1) at a substrate-to-enzyme mass ratio of 40:1 to 60:1.

Preferably, the fermenting in step (2) is performed at a temperature of 15 to 30° C. for 5 to 10 days.

In addition, the present invention provides a method of preparing an anthocyanin oligomer, comprising fermenting an anthocyanin monomer by adding the anthocyanin monomer with a coenzyme, which is present in a culture media of an *Aspergillus* sp. strain and contains glucosidase as an active ingredient, and with the multi-enzyme complex containing a wide range of carbohydrases (Viscozyme® L).

According to the present invention, in order to overcome contamination problems during the culturing process using *Aspergillus niger*, a coenzyme of *Aspergillus niger* is extracted and the fermentation process is performed using the same, whereby an anthocyanin oligomer characterized by reduced concern of contamination and superior radical-scavenging effects, compared to existing anthocyanin monomers, can be produced.

Also, an anthocyanin oligomer, obtained through fermentation using glucosidase as an enzyme contained in the coenzyme, can exhibit excellent fermentation efficiency and radical-scavenging ability, and polymerization of the anthocyanin oligomer can be confirmed even upon the fermentation of the enzyme including glucosidase.

DETAILED DESCRIPTION

Hereinafter, a detailed description will be given of the present invention.

The present invention pertains to a method of preparing an anthocyanin oligomer, comprising (1) isolating a water-soluble coenzyme from a culture media of an *Aspergillus* sp. strain and (2) fermenting an anthocyanin monomer with the coenzyme isolated in step (1).

The *Aspergillus* sp. strain in step (1) is preferably *Aspergillus niger*.

The strain in step (1) is preferably cultured at a temperature of 15 to 30° C. for 4 to 8 days, and more preferably at 25° C. for 5 days.

The coenzyme in step (1) is preferably isolated as an enzyme by adding the culture media with an organic solvent to give a precipitate and dissolving the precipitate in distilled water.

The fermenting in step (2) is preferably includes mixing the anthocyanin monomer and distilled water at a mass ratio of 1:8 to 1:15 to prepare an anthocyanin monomer solution, after which mixing the anthocyanin monomer solution and the coenzyme isolated in step (1) at a substrate-to-enzyme mass ratio of 40:1 to 60:1. The substrate is an anthocyanin monomer. More preferably, the anthocyanin monomer and distilled water are mixed at a mass ratio of 1:10 to prepare an anthocyanin monomer solution, after which the anthocyanin monomer solution and the coenzyme isolated in step (1) are mixed at a mass ratio of 50:1.

The fermenting in step (2) is preferably at a temperature of 15 to 30° C. for 5 to 10 days, and more preferably at 25° C. for 7 days. The amount of the anthocyanin oligomer that is synthesized is increased up to 7 days, but does not change further even over time under conditions after 8 days.

The coenzyme isolated in step (1) contains glucosidase as an active ingredient.

In addition, the present invention pertains to a method of preparing an anthocyanin oligomer, comprising fermenting an anthocyanin monomer by adding the anthocyanin monomer with a coenzyme, which is present in a culture media of an *Aspergillus* sp. strain and contains glucosidase as an active ingredient, and with the multi-enzyme complex containing a wide range of carbohydrases (Viscozyme® L).

A better understanding of the present invention will be given through the following examples, which are merely set forth to illustrate the present invention but are not to be construed as limiting the scope of the present invention, as will be apparent to those skilled in the art.

Figure 1:
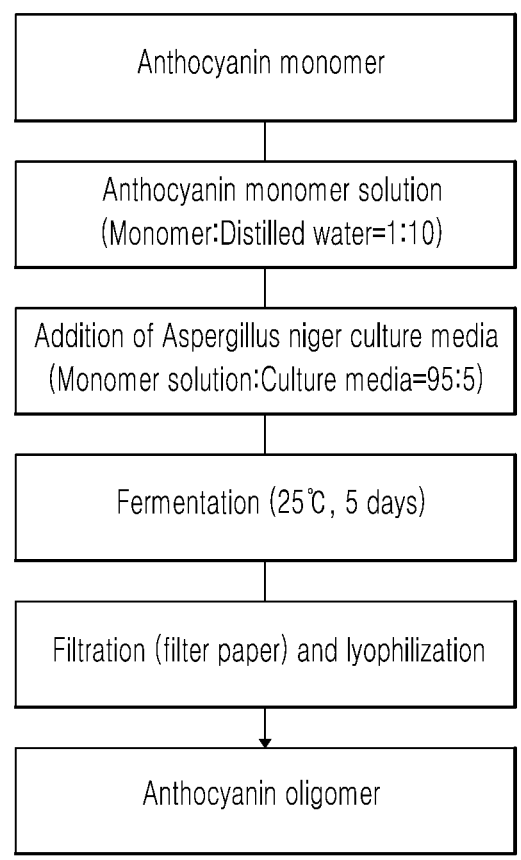
FIG. 1 shows a process of preparing an anthocyanin oligomer by fermenting an anthocyanin monomer with an *Aspergillus niger* culture media in Example 1 of the present invention.

Example 1. Evaluation of Ability of *Aspergillus* Sp. Strain Culture Media to Synthesize Oligomer As summarized in FIG. 1, an anthocyanin monomer and distilled water were mixed at a mass ratio of 1:10 to give an anthocyanin monomer solution. Then, the anthocyanin monomer solution and an *Aspergillus niger* strain culture media were mixed at a mass ratio of 95:5 and fermented at 25° C. for 5 days. The strain culture media was made by culturing an *Aspergillus niger* strain in 1 L of a medium solution at 25° C. for 5 days.

After the fermentation, a filtration process was performed using filter paper, whereby materials other than anthocyanin, such as the strain and the like, were filtered and thus the anthocyanin oligomer was isolated and lyophilized, thereby obtaining an anthocyanin oligomer. In order to purify the anthocyanin oligomer, filtration is preferably conducted using a tubular, capillary, coiled spiral, or plane membrane.

Figure 2:
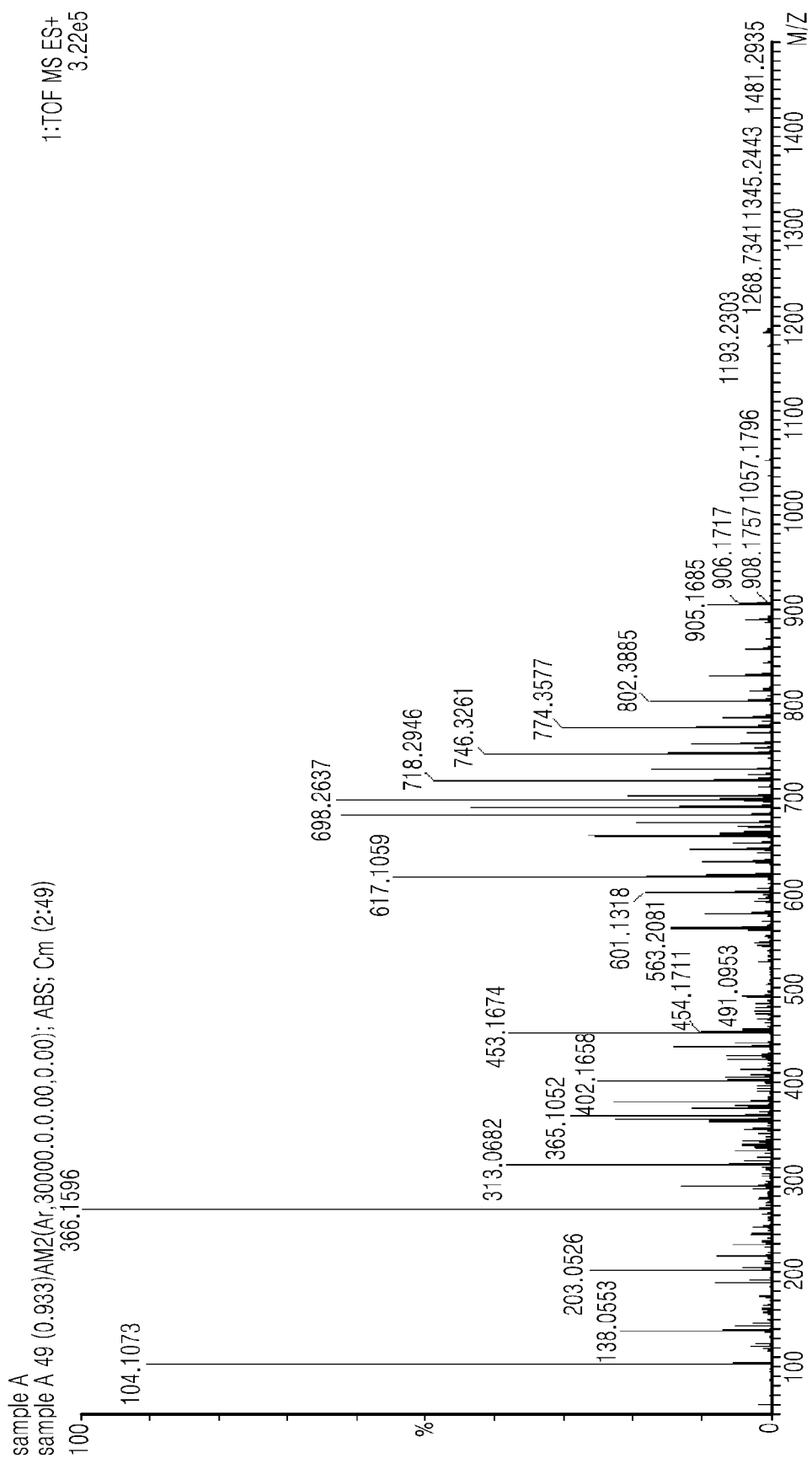
FIG. 2 is a graph showing the results of ESI mass spectrometry of an anthocyanin monomer serving as a control in Example 1 of the present invention.
Figure 3:
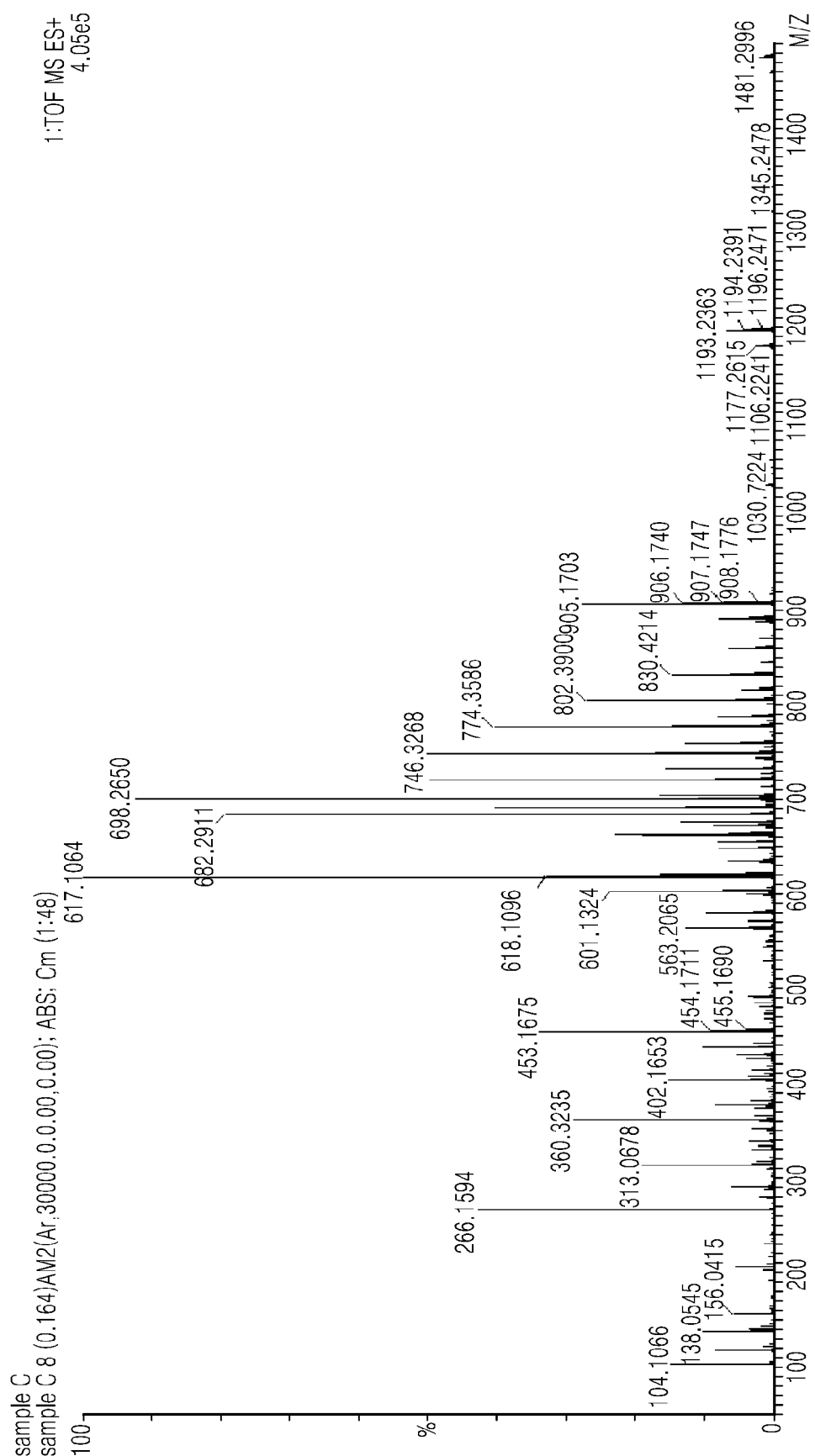
FIG. 3 is a graph showing whether synthesis of an anthocyanin oligomer occurred in Example 1 of the present invention through ESI mass spectrometry.

An anthocyanin monomer serving as a control was subjected to peak observation through ESI mass spectrometry. As shown in FIG. 2, the peak near the molecular weight of 300 was very high. However, based on the results of peak observation of the obtained anthocyanin oligomer through ESI mass spectrometry, as shown in FIG. 3, a high peak was observed near a molecular weight of 600, and peaks were also observed near 900 and 1200. This means that the anthocyanin monomer was fermented and thus converted into an anthocyanin oligomer, such as a dimer, a trimer, a tetramer, etc., from which the anthocyanin oligomer can be found to be synthesized.

Figure 4:
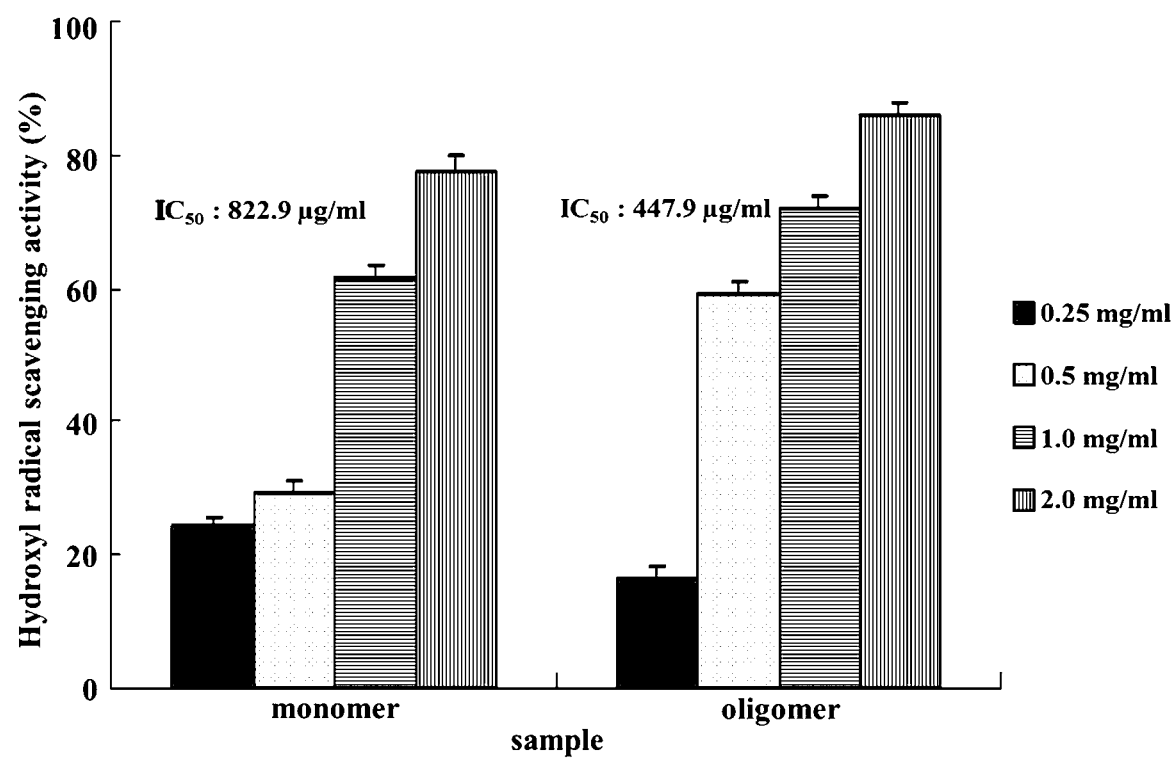
FIG. 4 is a graph showing the hydroxyl radical-scavenging activity of the anthocyanin oligomer synthesized by fermenting the anthocyanin monomer with an *Aspergillus niger* culture media in Example 1 of the present invention, depending on the concentration.

In order to compare the efficacy of the anthocyanin monomer with that of the anthocyanin oligomer, as shown in FIG. 4, hydroxyl radical-scavenging activity was tested using the monomer and the oligomer at different concentrations. Based on the test results, the inhibitory concentration ($IC_{50}$) of the oligomer was only about half that of the monomer, from which the anthocyanin oligomer can be found to exhibit radical-scavenging activity even at a low concentration.

Figure 5:
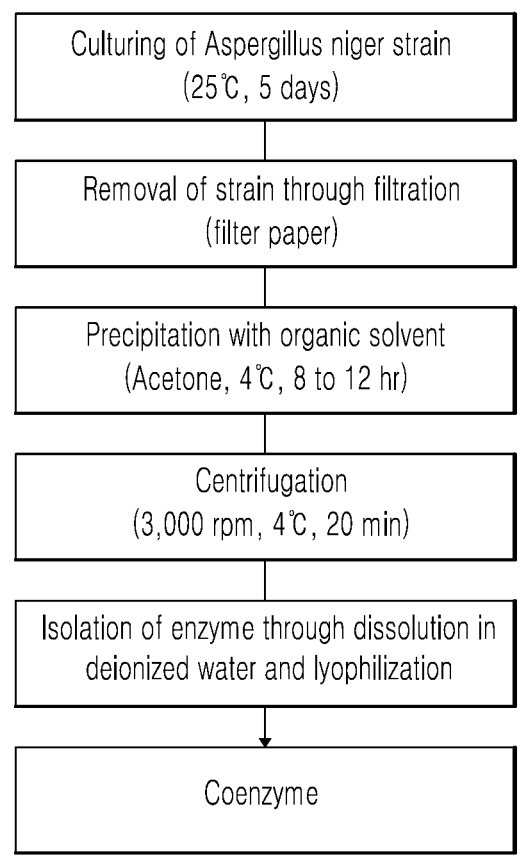
FIG. 5 shows a process of obtaining a coenzyme from an *Aspergillus niger* culture media in Example 2 of the present invention.

Example 2. Evaluation of Ability of Coenzyme Obtained from *Aspergillus* sp. Strain Culture Media to Synthesize Oligomer As summarized in FIG. 5, in order to obtain a coenzyme from an *Aspergillus niger* strain culture media, an *Aspergillus niger* strain was cultured in 2 L of a medium solution at 25° C. for 5 days, thus affording a culture media, after which the strain was removed through filtration using filter paper and precipitation was performed at 4° C. for 8 to 12 hr by the addition of acetone. Thereafter, centrifugation was performed at 3000 rpm for 20 min to give a culture precipitate, and the enzyme of the culture precipitate, which was dissolved in deionized water, was isolated and lyophilized, whereby the coenzyme was prepared.

Figure 6:
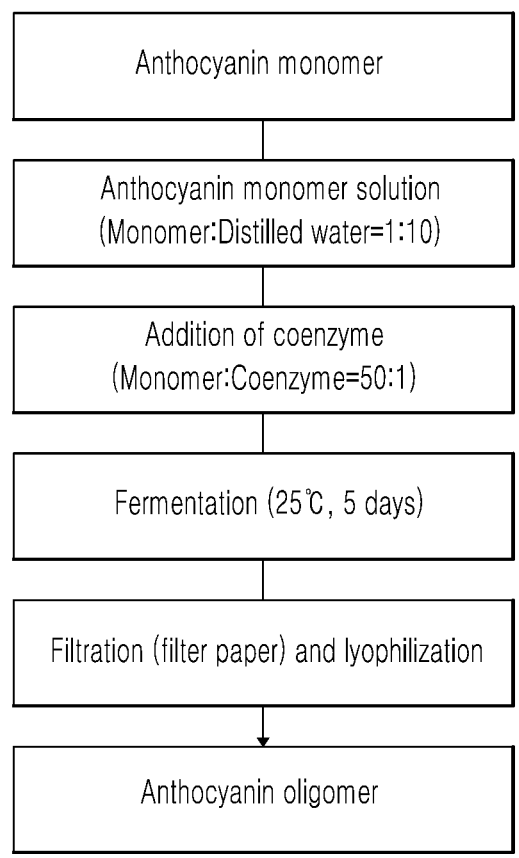
FIG. 6 shows a process of preparing an anthocyanin oligomer by fermenting an anthocyanin monomer with the coenzyme obtained from *Aspergillus niger* in Example 2 of the present invention.

Next, as summarized in FIG. 6, the anthocyanin monomer and distilled water were mixed at a mass ratio of 1:10 to give an anthocyanin monomer solution. Furthermore, the anthocyanin monomer solution and the coenzyme were mixed at a mass ratio of 500:1 and fermented at 25° C. for 5 days.

After the fermentation, a filtration process was performed using filter paper, whereby materials other than anthocyanin were filtered and thus the anthocyanin oligomer was isolated and lyophilized, thereby obtaining an anthocyanin oligomer. In order to purify the anthocyanin oligomer, filtration is preferably conducted using a tubular, capillary, coiled spiral, or plane membrane.

Figure 7:
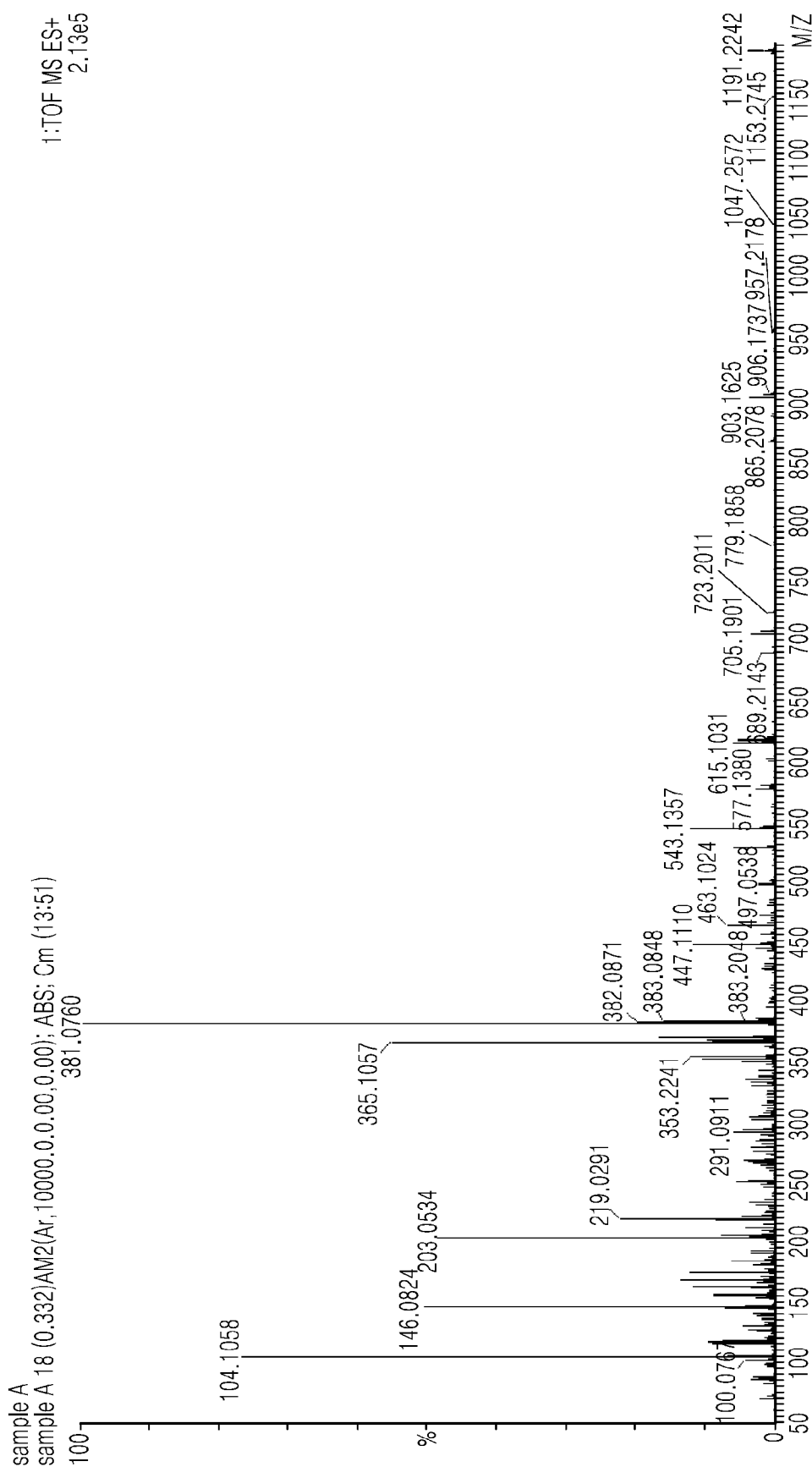
FIG. 7 is a graph showing the results of ESI mass spectrometry of an anthocyanin monomer serving as a control in Example 2 of the present invention.
Figure 8:
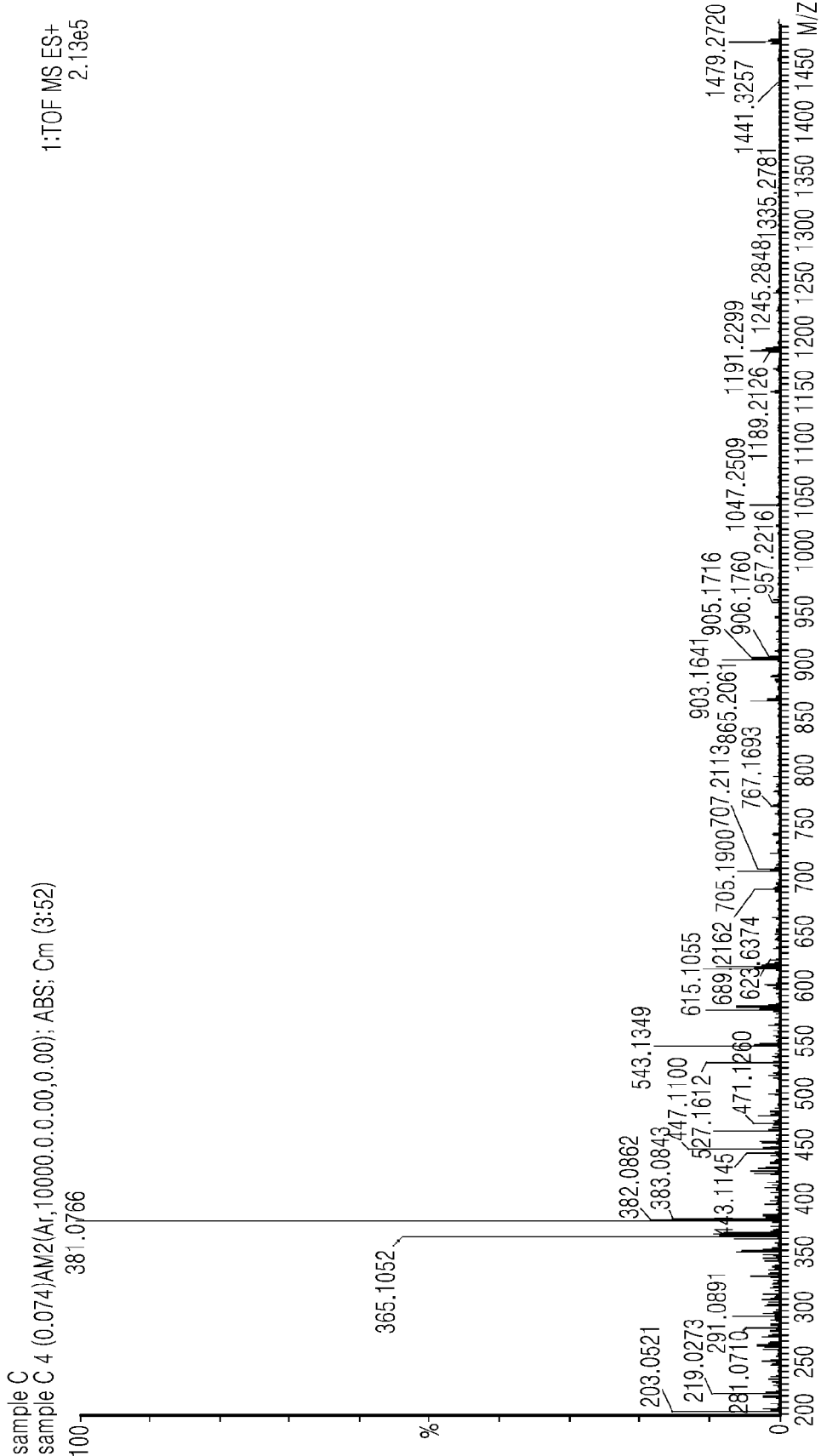
FIG. 8 is a graph showing whether synthesis of an anthocyanin oligomer occurred in Example 2 of the present invention through ESI mass spectrometry.

An anthocyanin monomer serving as a control was subjected to peak observation through ESI mass spectrometry. The results are shown in FIG. 7. Based on the results of peak observation of the obtained anthocyanin oligomer through ESI mass spectrometry, as shown in FIG. 8, high peaks were observed near the molecular weights of 600, 900 and 1200 compared to the results shown in FIG. 7. This means that the anthocyanin monomer was fermented and thus converted into an anthocyanin oligomer, such as a dimer, a trimer, a tetramer, etc., from which the anthocyanin oligomer can be found to be synthesized.

Figure 9:
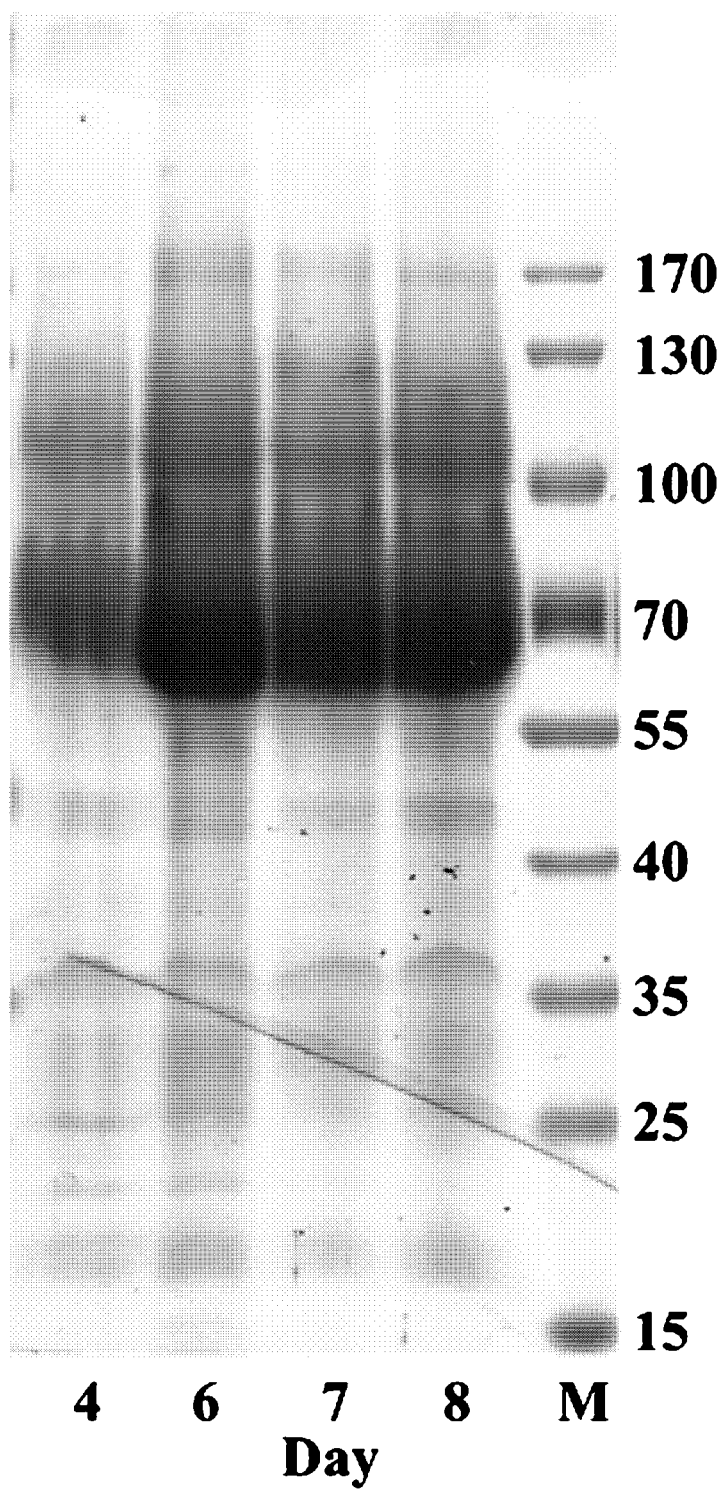
FIG. 9 is an SDS-PAGE image showing the expression of an *Aspergillus niger* coenzyme protein depending on the culturing period in Example 2 of the present invention.

In order to investigate the properties of the isolated coenzyme for synthesizing an anthocyanin oligomer and the culture conditions thereof, SDS-PAGE was performed. The results are shown in FIG. 9. Based on the results of SDS-PAGE for the amount of extracted coenzyme upon culturing for 4 to 8 days, the amount of the coenzyme that was extracted was similar even over time under conditions of 6 to 8 days. Thus, in order to prepare the coenzyme necessary to synthesize an anthocyanin oligomer, culturing *Aspergillus niger* for 5 days was found to be optimal.

Figure 10:
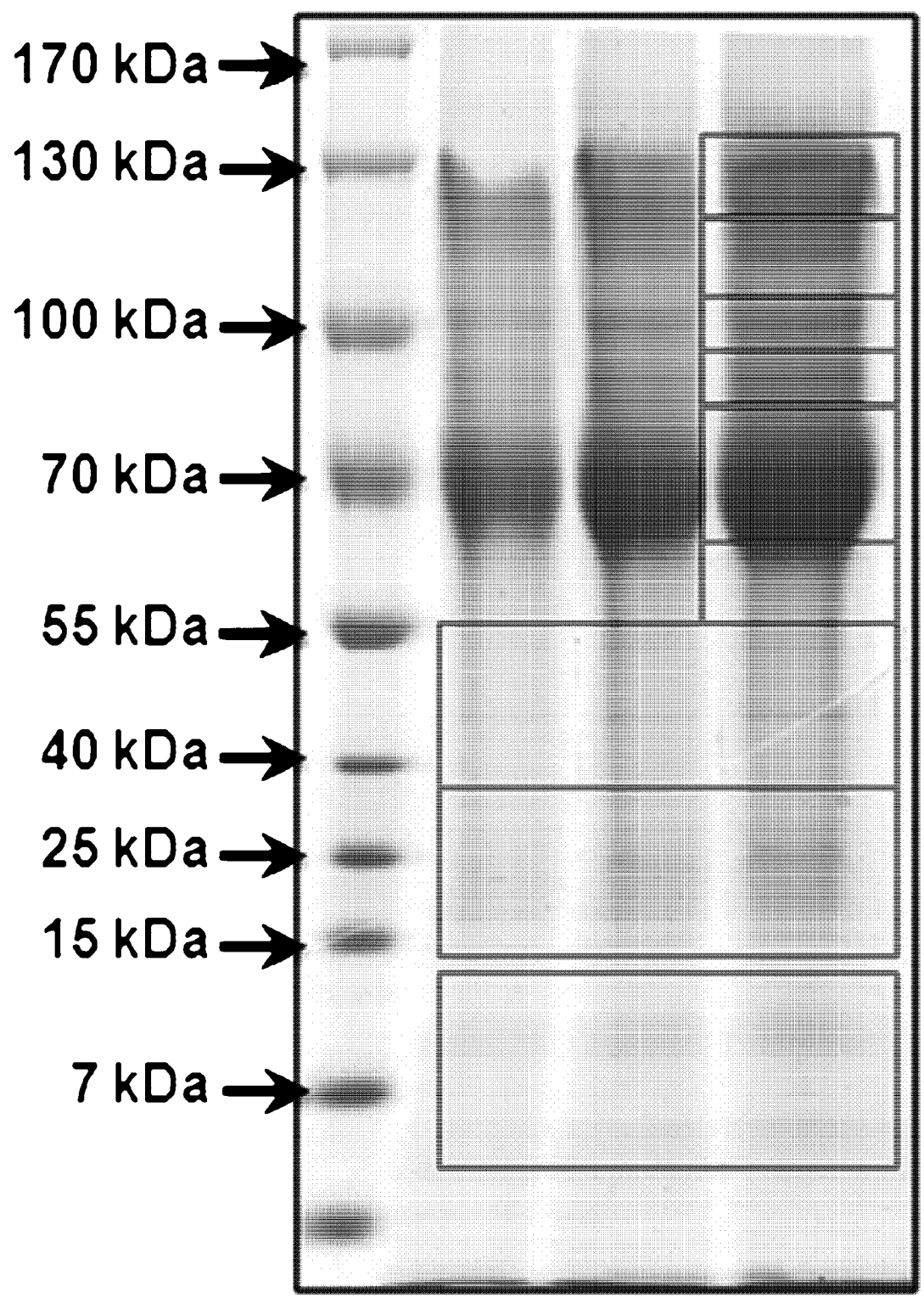
FIG. 10 is an SDS-PAGE image for analysis of the enzyme contained in the *Aspergillus niger* coenzyme in Example 2 of the present invention.

As indicated by the rectangle in FIG. 10, nine thin fragments were obtained, digested with trypsin protease, and analyzed by LC-MS/MS in a Q-STAR Pulsar ESI-hybrid Q-TOF instrument. As results thereof, tens of proteins were validated and MS/MS spectrum peaks thereof were analyzed with Analyst QS (v1.1, Applied Biosystems) to identify proteins. The identified proteins are shown in the following Tables. *Aspergillus niger* is currently receiving attention as industrially useful model fungi, and these fungi are known to secrete hydrolytic proteins which are very suitable for the production of various food additives, pharmaceuticals and industrial enzymes. Among the identified proteins of Tables 1 and 2 below, some proteins expected to be involved in anthocyanin oligomer metabolism were selected and represented as italic types.

TABLE 1

| Gene I.D. | Protein name | Probability | Molecular Weight |
|---|---|---|---|
| gi|224027 | *glucoamylase G1* | 627 | 65448 |
| gi|134081727 | unnamed protein product [*Aspergillus niger*] | 274 | 75190 |
| gi|765328 | acid phosphatase, orthophosphoric monoester phosphohydrolase, APase {EC 3.1.3.2} [*Aspergillus ficuum*, NRRL 3135, Peptide, 583 aa] | 265 | 64211 |
| gi|257187 | alpha-glucosidase P2 subunit, ANP P2 subunit {EC 3.2.1.20} [*Aspergillus niger*, Peptide, 719 aa] | 181 | 79656 |
| gi|2344 | *preproglucoamylase G2 [Aspergillus niger]* | 531 | 56695 |
| gi|145242978 | hypothetical protein ANI_1_1546094 [*Aspergillus niger* CBS 513.88] | 351 | 59208 |
| gi|145231236 | *phospholipase C PLC-C [Aspergillus niger* CBS 513.88] | 410 | 49652 |
| gi|145235505 | serine carboxypeptidase [*Aspergillus niger* CBS 513.88] | 297 | 62560 |
| gi|145252338 | *phosphatidylglycerol specific phospholipase [Aspergillus niger* CBS 513.88] | 261 | 53895 |
| gi|4185610 | phytase [*Aspergillus niger*] | 218 | 50997 |
| gi|145241119 | 3-phytase B [*Aspergillus niger* CBS 513.88] | 256 | 52453 |
| gi|145241490 | 1,3-beta-glucanosyltransferase gel3 [*Aspergillus niger* CBS 513.88] | 161 | 56721 |

TABLE 1-continued

| Gene I.D. | Protein name | Probability | Molecular Weight |
|---|---|---|---|
| gi\|83655609 | acid phosphatase [*Aspergillus niger*] | 142 | 52725 |
| gi\|145242970 | hypothetical protein ANI_1_1540094 [*Aspergillus niger* CBS 513.88] | 128 | 45753 |
| gi\|145256696 | protein ecm33 [*Aspergillus niger* CBS 513.88] | 125 | 41026 |
| gi\|317026828 | serine-type carboxypeptidase F [*Aspergillus niger* CBS 513.88] | 118 | 57756 |
| gi\|145248273 | polyamine oxidase [*Aspergillus niger* CBS 513.88] | 110 | 58728 |
| gi\|145248205 | aspartic-type endopeptidase opsB [*Aspergillus niger* CBS 513.88] | 104 | 50958 |
| gi\|145234270 | glutaminase GtaA [*Aspergillus niger* CBS 513.88] | 99 | 75470 |
| gi\|350633205 | hypothetical protein ASPNIDRAFT_55058 [*Aspergillus niger* ATCC 1015] | 87 | 22487 |
| gi\|350631594 | hypothetical protein ASPNIDRAFT_53033 [*Aspergillus niger* ATCC 1015] | 63 | 57162 |
| gi\|145235707 | FAD binding domain protein [*Aspergillus niger* CBS 513.88] | 59 | 61292 |
| gi\|145233743 | alpha-galactosidase B [*Aspergillus niger* CBS 513.88] | 392 | 48796 |
| gi\|317031802 | histidine acid phosphatase [*Aspergillus niger* CBS 513.88] | 153 | 53047 |

TABLE 2

| gi\|317025164 | aspartic endopeptidase (AP1) [*Aspergillus niger* CBS 513.88] | 483 | 46701 |
|---|---|---|---|
| gi\|145242664 | sulphydryl oxidase [*Aspergillus niger* CBS 513.88] | 264 | 43471 |
| gi\|74626383 | RecName: Full = Probable alpha-galactosidase B; AltName: Full = Melibiase B; Flags: Precursor | 175 | 48753 |
| gi\|134083538 | unnamed protein product [*Aspergillus niger*] | 173 | 45226 |
| gi\|400801 | RecName: Full = Pectin lyase A; Short = PLA; AltName: Full = Pectin lyase II; Short = PLII; Flags: Precursor | 135 | 39830 |
| gi\|145235303 | hypothetical protein ANI_1_496034 [*Aspergillus niger* CBS 513.88) | 103 | 52301 |
| gi\|134055991 | unnamed protein product [*Aspergillus niger*] | 85 | 41620 |
| gi\|134076313 | unnamed protein product [*Aspergillus niger*] | 85 | 45581 |
| gi\|145251519 | phosphoglycerate mutase family protein [*Aspergillus niger* CBS 513.88] | 79 | 19282 |
| gi\|350633205 | hypothetical protein ASPNIDRAFT_55058 [*Aspergillus niger* ATCC 1015] | 73 | 22487 |
| gi\|145232359 | endopolygalacturonase C [*Aspergillus niger* CBS 513.88] | 241 | 37796 |
| gi\|145235523 | glucan endo-1,3-beta-glucosidase eglC [*Aspergillus niger* CBS 513.88] | 129 | 46778 |
| gi\|145230419 | glycosidase crf1 [*Aspergillus niger* CBS 513.88] | 107 | 39862 |
| gi\|129935 | RecName: Full-Endopolygalacturonase II; Short = EPG-II; AltName: Full = Pectinase 2; AltName: Full = Polygalacturonase II; Short = PG-II; AltName: Full = Polygalacturonase X2; Flags: Precursor | 89 | 37489 |
| gi\|133176 | RecName: Full = Ribonuclease M; Short = RNase M | 89 | 26590 |
| gi\|134055750 | unnamed protein product [*Aspergillus niger*] | 84 | 27072 |
| gi\|145229151 | endo-1,3(4)-beta-glucanase [*Aspergillus niger* CBS 513.88] | 83 | 46311 |
| gi\|134075575 | hypothetical protein An07g00170 [*Aspergillus niger*] | 69 | 90993 |
| gi\|134083538 | unnamed protein product [*Aspergillus niger*] | 67 | 45226 |
| gi\|145252266 | GPI anchored cell wall protein [*Aspergillus niger* CBS 513.88] | 64 | 19022 |
| gi\|83638302 | xylanase [*Aspergillus phoenicis*] | 117 | 10944 |
| gi\|350633205 | hypothetical protein ASPNIDRAFT_55058 [*Aspergillus niger*ATCC 1015] | 92 | 22487 |

Figure 11:
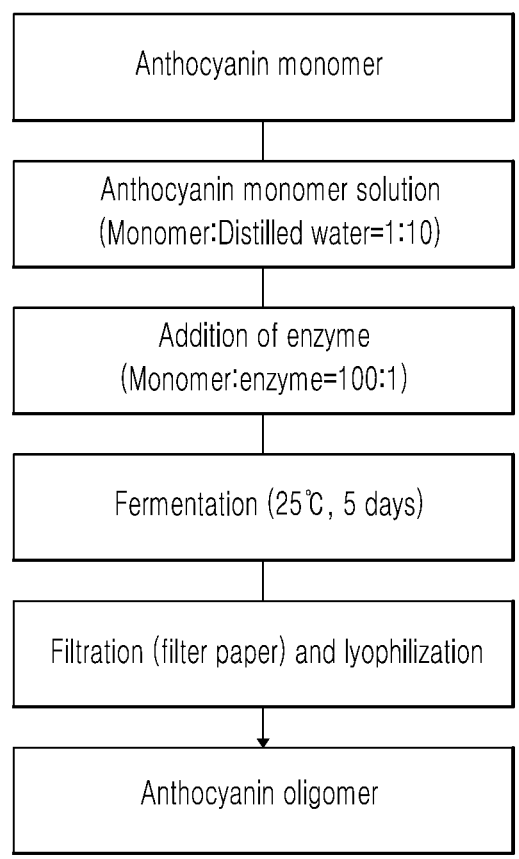
FIG. 11 shows a process of preparing an anthocyanin oligomer by fermenting an anthocyanin monomer with glucosidase, which is an enzyme obtained from *Aspergillus niger*, and with the multi-enzyme complex containing a wide range of carbohydrases (Viscozyme® L) in Example 3 of the present invention.

Example 3. Evaluation of Ability of Glucosidase in Coenzyme Obtained from *Aspergillus* sp. Strain Culture Media and of the Multi-Enzyme Complex Containing a Wide Range of Carbohydrases (Viscozyme® L) to Synthesize Oligomer As summarized in FIG. 11, an anthocyanin monomer and distilled water were mixed at a mass ratio of 1:10 to give an anthocyanin monomer solution. Then, the anthocyanin monomer solution was mixed with each of glucosidase, which is an enzyme isolated from the *Aspergillus niger* strain coenzyme, and the multi-enzyme complex containing a wide range of carbohydrases (Viscozyme® L), at a mass ratio of 1000:1 and 500:1, respectively ("100:1" of FIG. 11 is the mass ratio of the anthocyanin monomer itself, rather than the solution, to the enzyme, and the multi-enzyme complex containing a wide range of carbohydrases (Viscozyme® L) was used in double the amount in order to ensure similar effects due to the high enzyme efficiency of glucosidase), and fermented at 25° C. for 5 days.

The multi-enzyme complex containing a wide range of carbohydrases (Viscozyme® L) is an enzyme that includes glucosidase and is commercially available.

After the fermentation, a filtration process was performed using filter paper, whereby materials other than anthocyanin were filtered and thus the anthocyanin oligomer was isolated and lyophilized, thereby obtaining an anthocyanin oligomer. In order to purify the anthocyanin oligomer, filtration is preferably conducted using a tubular, capillary, coiled spiral, or plane membrane.

Figure 12:
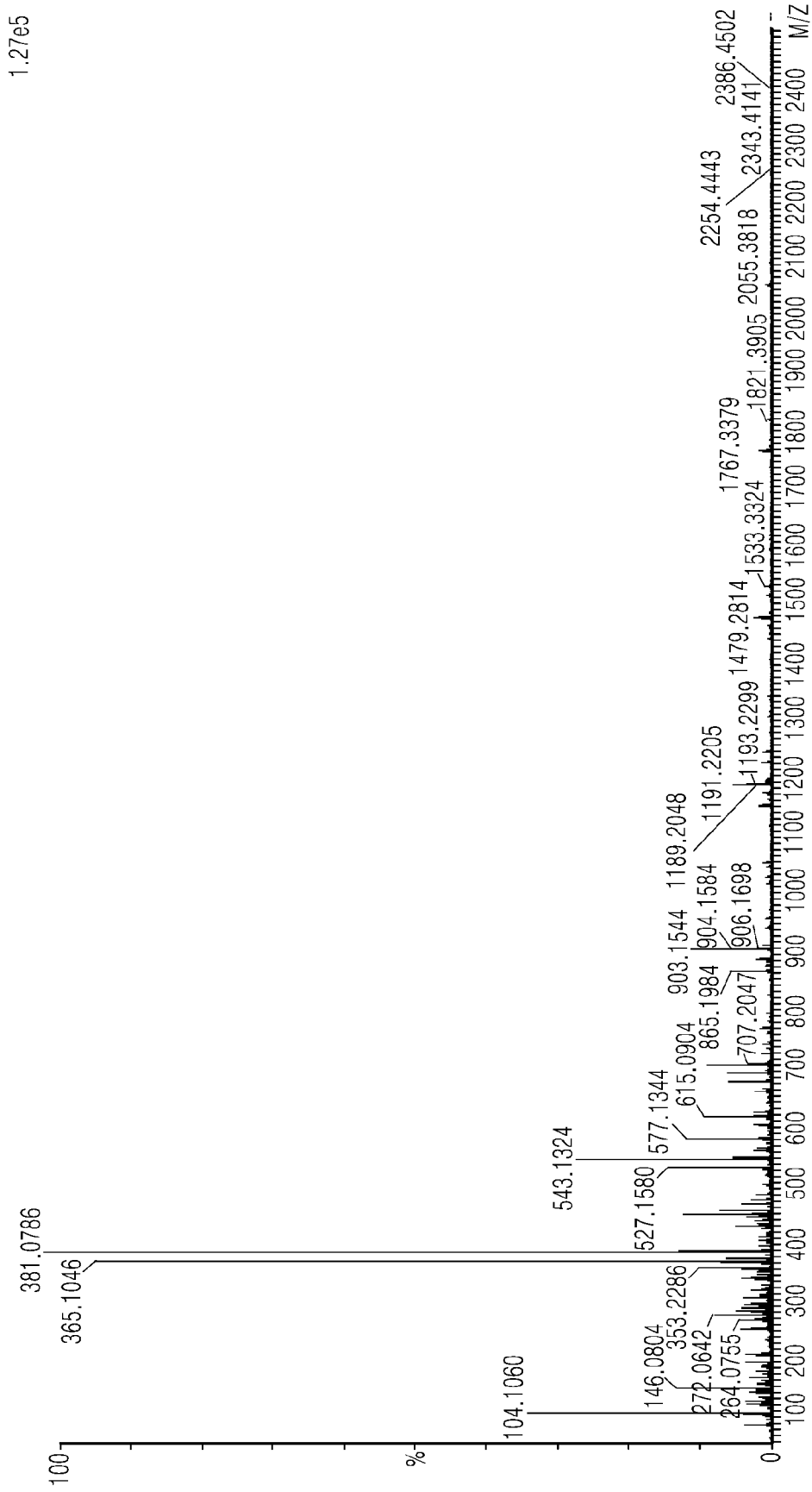
FIG. 12 shows the results of ESI mass spectrometry of an anthocyanin monomer serving as a control in Example 3 of the present invention.
Figure 13:
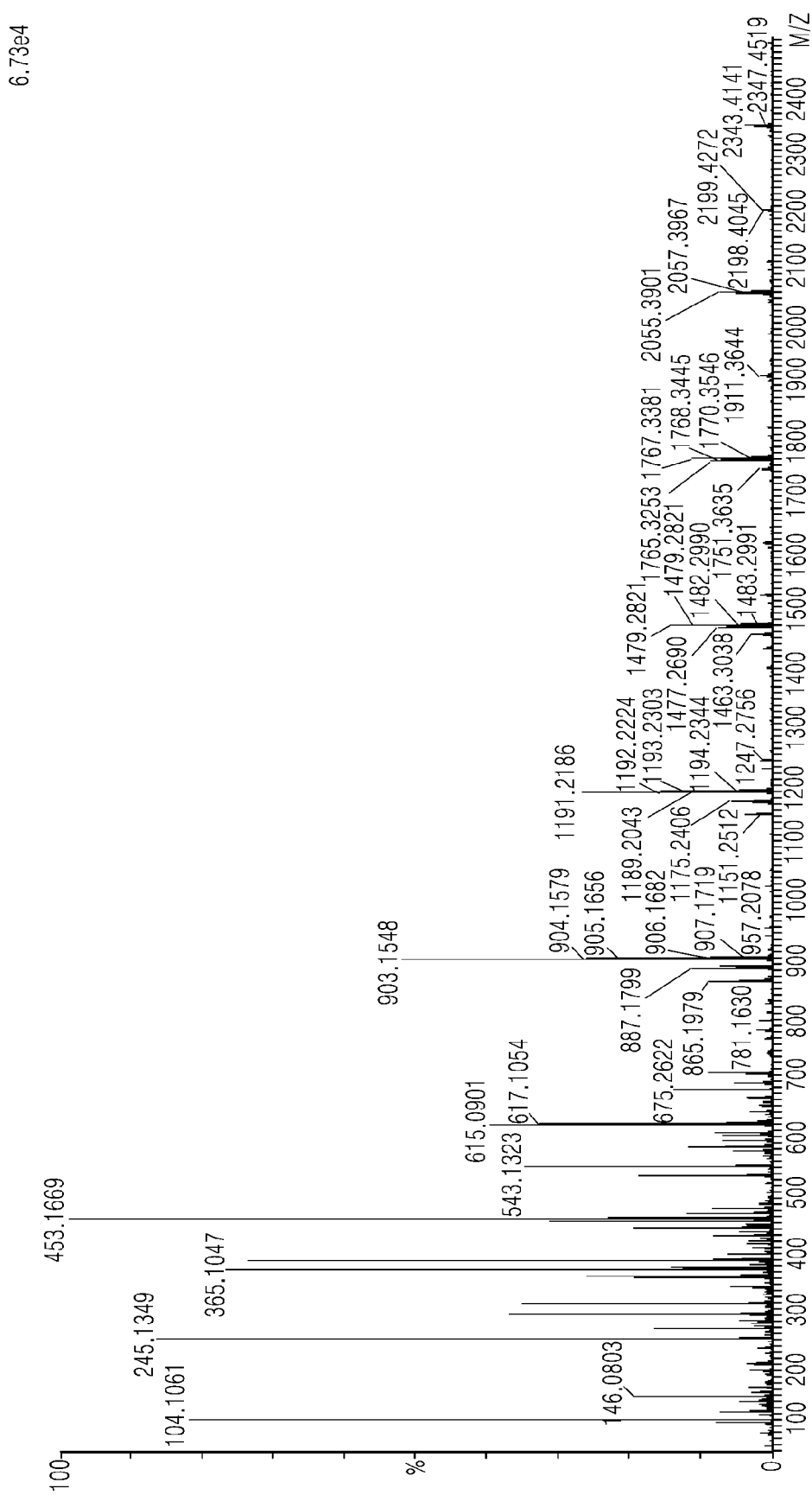
FIG. 13 is a graph showing whether synthesis of an anthocyanin oligomer occurred when using glucosidase as an enzyme in Example 3 of the present invention through ESI mass spectrometry.
Figure 14:
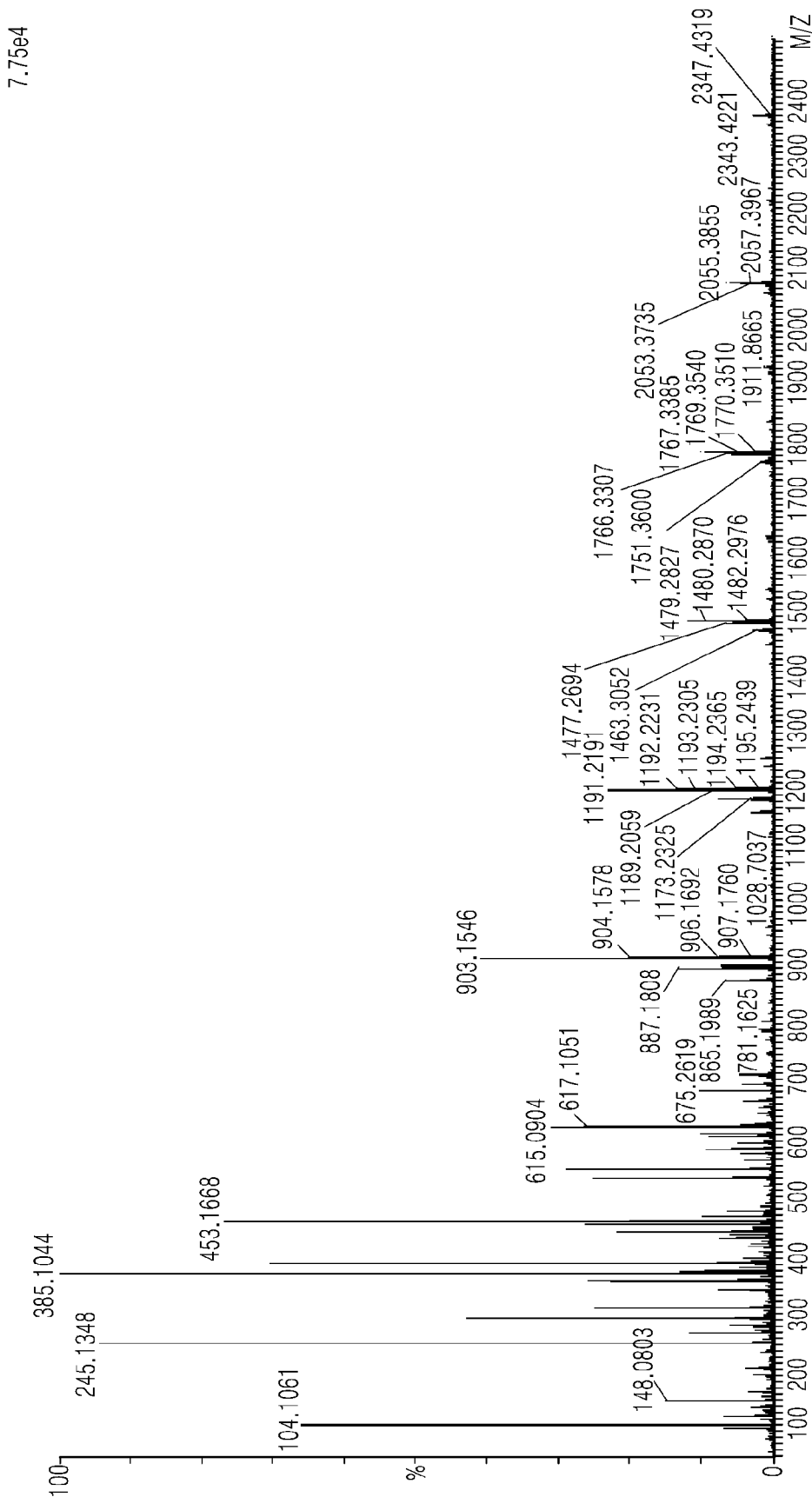
FIG. 14 is a graph showing whether synthesis of an anthocyanin oligomer occurred when using the multi-enzyme complex containing a wide range of carbohydrases (Viscozyme® L) as an enzyme in Example 3 of the present invention through ESI mass spectrometry.

An anthocyanin monomer serving as a control was subjected to peak observation through ESI mass spectrometry. The results are shown in FIG. 12. However, based on the results of peak observation through ESI mass spectrometry of the anthocyanin oligomers obtained using glucosidase, which is an enzyme isolated from the *Aspergillus niger* strain coenzyme, and the multi-enzyme complex containing a wide range of carbohydrases (Viscozyme® L), as shown in FIGS. 13 and 14, high peaks were observed near molecular weights of 600, 900 and 1200 compared to the results shown in FIG. 12. This means that the anthocyanin monomer was fermented and thus converted into an anthocyanin oligomer, such as a dimer, a trimer, a tetramer, etc., from which the anthocyanin oligomer can be found to be synthesized. Moreover, the amount of the synthesized oligomer was high when using glucosidase as the enzyme (FIG. 13) compared to when using the multi-enzyme complex containing a wide range of carbohydrases (Viscozyme® L) (FIG. 14).

Figure 15:
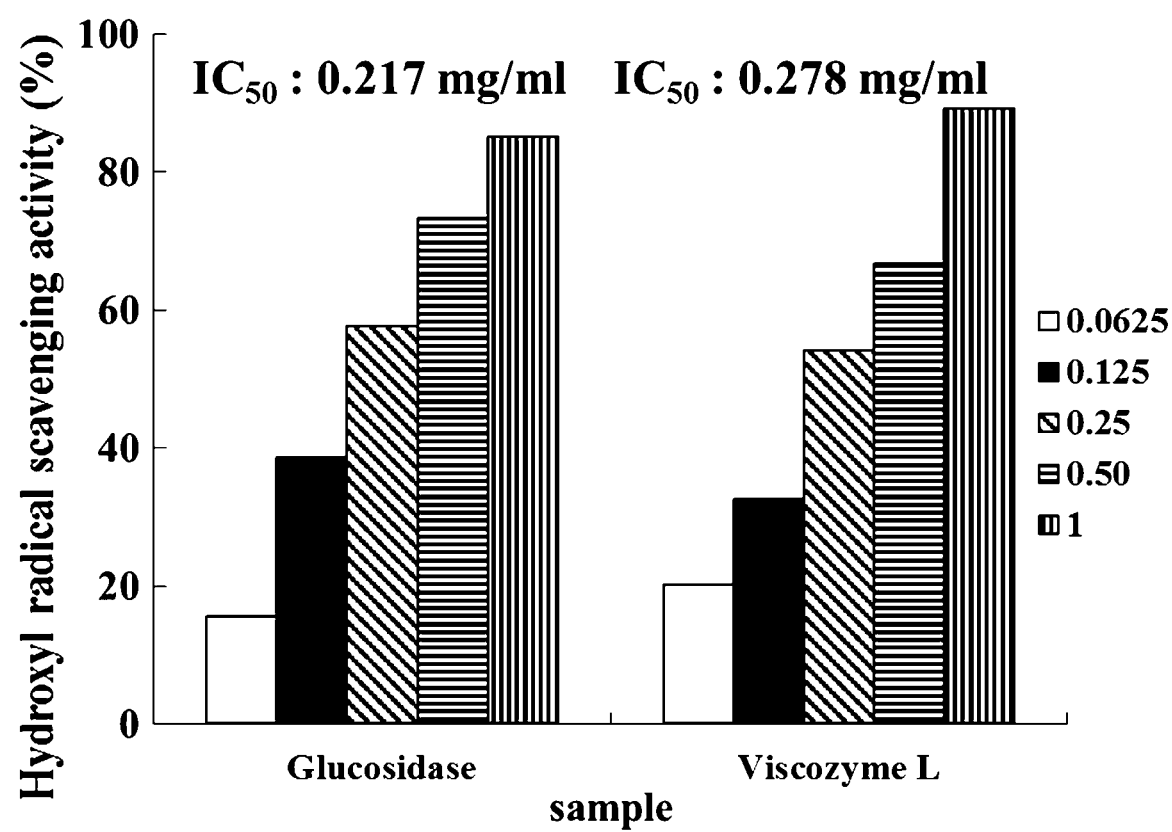
FIG. 15 is a graph showing the hydroxyl radical-scavenging activity of two kinds of anthocyanin oligomers prepared through fermentation with glucosidase, which is an enzyme obtained from *Aspergillus niger*, and with the multi-enzyme complex containing a wide range of carbohydrases (Viscozyme® L) in Example 3 of the present invention, depending on the concentration.

In order to compare the efficacies of the anthocyanin oligomers obtained using individual enzymes, as shown in FIG. 15, the oligomer obtained using glucosidase and the oligomer obtained using the multi-enzyme complex containing a wide range of carbohydrases (Viscozyme® L) were set to different concentrations and tested for hydroxyl radical-scavenging activity. Based on the test results, the oligomer obtained using glucosidase exhibited an inhibitory concentration ($IC_{50}$) of 0.217 mg/ml, which is much lower than 0.278 mg/ml, which is the inhibitory concentration ($IC_{50}$) of the oligomer obtained using the multi-enzyme complex containing a wide range of carbohydrases (Viscozyme® L), and was thus concluded to exhibit radical-scavenging activity even at a low concentration.

Having described specific portions of the present invention in detail, those skilled in the art will appreciate that these specific embodiments are merely preferred embodiments and that the scope of the present invention is not limited thereby. Accordingly, the actual scope of the present invention will be defined by the appended claims and equivalents thereof.

The invention claimed is:

1. A method of preparing an anthocyanin oligomer, comprising:
   (i) mixing an anthocyanin monomer and distilled water at a mass ratio of 1:8 to 1:15 to prepare an anthocyanin monomer solution;
   (ii) mixing the anthocyanin monomer solution and a multi-enzyme complex comprising arabanase, cellulase, β-glucanase, hemicellulase, and xylanase, the multi-enzyme complex being available under the trade name Viscozyme® L, at a mass ratio of 500:1;
   (iii) fermenting the solution prepared in step (ii) at a temperature of 15° C. to 30° C. for 5 days to 10 days; and
   (iv) filtrating the fermented solution using filter paper to obtain the anthocyanin oligomer.

* * * * *